United States Patent [19]

Reinhardt

[11] Patent Number: 5,048,513

[45] Date of Patent: Sep. 17, 1991

[54] BANDAGE CONSISTING OF ELASTICATED TEXTILE MATERIAL

[75] Inventor: Holger Reinhardt, Kampen, Fed. Rep. of Germany

[73] Assignee: Bauerfeind GmbH & Co., Kempea, Fed. Rep. of Germany

[21] Appl. No.: 410,652

[22] Filed: Sep. 21, 1989

[30] Foreign Application Priority Data

Sep. 23, 1988 [DE] Fed. Rep. of Germany ....... 3832438

[51] Int. Cl.$^5$ ............................................. C08G 18/10
[52] U.S. Cl. .................................... 128/156; 128/155
[58] Field of Search ............. 128/155, 156, 157, 159, 128/160, 163, 167, 165, 169, 890, 891, 899

[56] References Cited

U.S. PATENT DOCUMENTS

| | | | |
|---|---|---|---|
| 1,845,630 | 2/1932 | Scholl | 128/155 |
| 2,560,712 | 7/1951 | Bell | 128/155 |
| 2,649,088 | 8/1953 | Sigg | 128/156 |
| 3,125,093 | 7/1961 | Hutchins | 128/169 X |
| 3,156,242 | 11/1964 | Crowe | 128/156 |
| 3,872,862 | 3/1975 | Hume | 128/156 X |
| 3,972,328 | 8/1976 | Chen | 120/156 |
| 4,727,868 | 3/1988 | Szycher et al. | 128/156 |
| 4,753,231 | 6/1988 | Lang et al. | 128/155 X |

*Primary Examiner*—Alan Cannon
*Assistant Examiner*—N. Paul

[57] ABSTRACT

A bandage consisting of elastic textile material, e.g. stocking, which is provided with a cushion covered by an overlay consisting of the same or similar textile material and which is secured to the textile material of the bandage by means of a border which projects over the cushion. The overlay is provided with, on the side facing the cushion, an elastic thermoplastic synthetic coating which is adhered to the textile material of the bandage in the region of the border areas by heating and whose softening temperature is below that of the textile material.

13 Claims, 1 Drawing Sheet

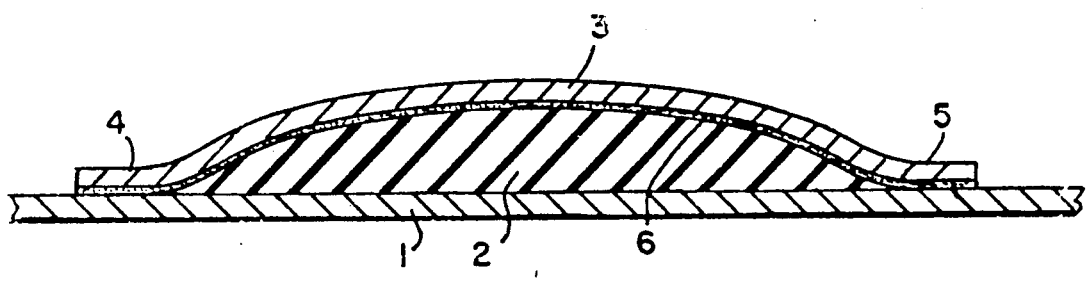

BANDAGE CONSISTING OF ELASTICATED TEXTILE MATERIAL

The invention applies to a bandage consisting of elasticated textile material, e.g. a stocking.

Such bandages are used in the treatment of joints, e.g. the knee or ankle joint, in which the bandage is provided with a cushion in order to avoid pressure points. Up until now the cushions have been fastened to the base material of the bandage, usually an elastic, knitted textile material by sewing on an overlay consisting of the same kind of textile material, whereby the overlay forms a border around the bandage which is sewed tightly to the base material, enclosing the cushion. So as not to interfere with the elasticity of the bandage, sewing stitches, e.g. zig-zag, are used which maintain a certain amount of elasticity within this border seam. It is, however, a well-known fact that the bandage loses a certain amount of elasticity in the area affected as a result of such seams, a result that is, of course, undesired.

The use of cushion material, e.g. for car seats, under overlays, as is described in the British Patent 1,100,553, is known. Here the cushion material is placed on a base material and covered by an overlay which is then welded together with the base material by the use of high frequency. A textile material coated with a layer of plastic can be used for the base material and for the overlay. The welding together then takes place in the area of the points of contact of the plastic coating.

Such a method of adhesion is inappropriate for the bandage in question because a pronounced reduction in elasticity results in the area of the welded seam insofar as the plastic coating permits elasticity at all, a point about which, however, nothing is disclosed in the above-mentioned British Patent 1,100,553.

It is the object of the invention to improve the fastening of the cushion to the bandage in such a way that hardly any loss in elasticity results in the area of the fastening.

As a result of the application of the elastic, thermoplastic synthetic coating on the side of the overlay facing the cushion, the overlay retains its elasticity in its full capacity, such that the elasticity of the overlay is not changed by the synthetic coating. This is also the case as far as the area of adhesion with the textile material of the bandage is concerned, since its elasticity properties are not changed by the heating of the synthetic material to its melting point nor by the its following setting. The adhesion with the textile material of the bandage only involves the joining of the coating with the threads of the textile material on its surface, without these being welded together, in which case they would lose their elasticity to a large extent. Softening of the textile material is here avoided by the fact that a synthetic substance is used for the overlay coating whose softening point lies below that of the textile material.

The heating of the synthetic coating is carried out effectively in a well-known way by the use of high frequency: here the textile material is laid, with the bandage and with the cushion and the overlay located on the top, onto a high frequency electrode adapted as a plate, upon which a further second high frequency electrode is then placed on the outline of the section one wishes to adhere. The materials lying there-between, namely the textile material of the bandage and the overlay of the synthetic coating act as insulators into which the desired heating enters as a result of the use of the high frequency, as is well-known.

The above-described formation of the bandage has, moreover, the advantage of resulting in a fundamental manufacturing advantage in comparison with the previously necessary sewing on of the overlay, since adhesion through heating constitutes a simple step forward in manufacturing which would be easy to automate.

A suitable synthetic coating to use is polyurethane which is well-know as having good elasticity properties.

It is possible to paint the synthetic coating onto the overlay, for which the synthetic material is first dissolved into a solvent which evaporates after being painted on. It is also possible, however, to spray the synthetic coating onto the overlay, in which above all, areas which will later come into contact with the cushion can be omitted, e.g. by use of a stencil. In this case the synthetic material does not impede the air and humidity permeability of the overlay which could lead to inconvenience especially where larger cushions are used.

It is, of course, also possible to use any other known method to apply the synthetic coating onto the overlay.

BRIEF DESCRIPTION OF THE DRAWINGS

An explanatory example of the invention is represented in the diagram.

It shows in section a part of a bandage with the textile base material 1, e.g. a knitted textile material, upon which the cushion 2 is placed. The cushion 2 can, e.g. be made out of an elasticated foam. The cushion 2 is covered by the overlay 3 of which only the border areas 4 and 5 project out over the cushion 2. The overlay 3 is provided with the synthetic coating 6 on the side facing the cushion 2, which is shown by the heavier line, and which has been adhered to the surface of the textile material 1 in the border areas 4 and 5 as a result of heating in these areas. The border areas 4 and 5 showing the adhesion 7, enclose completely or essentially completely the cushion 2, such that the latter is adhered to the textile base material securely. The areas of the adhesion 7 in the border areas 4 and 5 are shown by the heavier lines in those areas.

I claim:

1. A bandage formed of elastic textile material, said elastic textile material being provided with a cushion covered by an overlay of an elastic textile material and which is secured to the elastic textile material of the bandage by means of border areas which project over the cushion, characterized in that:
    the overlay (3) is provided, on the side facing the cushion (2), with an elastic thermoplastic synthetic coating (6), the softening temperature of said coating being less than that of said elastic textile material, said overlay being adhered to the elastic textile material (1) of the bandage in the region of the border areas (4, 5) by heating.

2. Bandage according to claim 1, characterized in that the synthetic coating (6) consists of polyurethane.

3. Bandage according to claim 1. characterized in that the synthetic coating (6) is painted onto the overlay (3).

4. Bandage according to claim 1, characterized in that the synthetic coating (6) is sprayed onto the overlay (3).

5. Bandage according to claim 2, characterized in that the synthetic coating (6) is painted onto the overlay (3).

6. Bandage according to claim 2, characterized in that the synthetic coating (6) is sprayed onto the overlay (3).

7. The bandage according to claim 1 wherein the elastic textile material is in the shape of a stocking.

8. A device adapted to engage a joint of a body, said device comprising:
- a bandage of elongated elastic textile material;
- an overlay disposed on said bandage, said overlay being formed of an elastic textile material as said bandage, said overlay further being secured to said bandage at it's border areas; and
- a cushion disposed within the border areas between said overlay and said bandage characterized in that an elastic thermoplastic synthetic coating is disposed on the elastic textile material of said overlay, said overlay being attached to said bandage by said coating, said coating having a softening point less than that of said elastic textile material and wherein said overlay is thermally fused to said bandage.

9. The device according to claim 8 wherein the synthetic coating is polyurethane.

10. The device according to claim 8 wherein the synthetic coating is painted onto the overlay.

11. The device according to claim 8 wherein the synthetic coating is sprayed onto the overlay.

12. The device according to claim 8 wherein the bandage is in a tubular form adapted to encircle a joint and the cushion and overlay is disposed on the inside of the tube.

13. The device according to claim 8 wherein the coating covers the threads of the overlay, but the overlay is not attached directly to the bandage.

* * * * *